(12) United States Patent
Kalder et al.

(10) Patent No.: US 6,447,795 B2
(45) Date of Patent: Sep. 10, 2002

(54) GEL FORMULATIONS CONTAINING INSECTICIDE

(75) Inventors: Dietmar Kalder, Langenfeld; Rolf Jung, Köln; Burkhard Mielke, Kürten, all of (DE)

(73) Assignee: Bayer Aktiengesellschaft (DE)

( * ) Notice: Subject to any disclaimer, the term of this patent is extended or adjusted under 35 U.S.C. 154(b) by 0 days.

(21) Appl. No.: 09/462,958

(22) PCT Filed: Jul. 8, 1998

(86) PCT No.: PCT/EP98/04253

§ 371 (c)(1),
(2), (4) Date: Jan. 14, 2000

(87) PCT Pub. No.: WO99/04629

PCT Pub. Date: Feb. 4, 1999

(30) Foreign Application Priority Data

Jul. 21, 1997 (DE) .......................................... 197 31 156

(51) Int. Cl.⁷ .......................................... A01N 25/18
(52) U.S. Cl. .......................... 424/411; 424/40; 424/43; 424/405; 424/409; 424/484; 424/485; 424/486; 424/DIG. 10; 514/65; 514/521; 514/531
(58) Field of Search ................. 424/405–407, 424/409, 411–421, DIG. 10, 484–486, 40, 43; 514/531, 65, 919, 519, 520, 521

(56) References Cited

U.S. PATENT DOCUMENTS 5,645,845 A 7/1997 Neumann et al. ........... 424/405

FOREIGN PATENT DOCUMENTS

| EP | 253640 | 1/1988 | .......... A01N/25/18 |
| EP | 0253640 | 1/1988 | |
| EP | 0693254 | 1/1996 | |
| EP | 693254 | 1/1996 | .......... A01N/53/06 |
| GB | 2022417 | 12/1979 | |
| GB | 2070933 | 3/1981 | .......... A01N/25/34 |
| GB | 1587396 | 4/1981 | |
| GB | 2153227 | 8/1985 | .......... A01N/25/18 |
| WO | 95/09604 | 4/1995 | ............ A61K/7/46 |
| WO | 9509604 | 4/1995 | |

OTHER PUBLICATIONS

Oleochemicals Specification Sheet, Guerbitol 32/36, downloaded from www.cognis.com, revision 2–10.1999, effective Nov. 1, 1999.

Oleochemicals Specification Sheet, Guerbitol 16, downloaded from www.cognis.com, revision 3–07.1999, effective Sep. 1, 1998.

*Primary Examiner*—Neil S. Levy

(57) ABSTRACT

The present invention relates to novel insecticidal gel formulations for the controlled and sustained release of insecticidally active compounds by means of a heat source.

15 Claims, No Drawings

GEL FORMULATIONS CONTAINING INSECTICIDE

The present invention relates to novel insecticidal gel formulations for the controlled and sustained release of insecticidal active compounds by means of a heat source. These novel gel formulations are characterized in that they comprise at least one type of insecticide and at least one vaporization-controlling substance (vaporization modifier), in combination with a solid suitable as a gel former.

The present invention is based on known gel formulations as described in EP 0 693 254, where insecticidally active compounds with novel, alternative solvents in combination with perfumes, colorants and auxiliaries are to display an optimum effect without decomposition for a relatively long period of time.

This novel active compound formulation is to be used in deep-drawn or cast containers made of polymer or metal, these containers being open or closed by means of suitable fabrics, films made of polymer, for example polypropylene film, or metal, which are permeable to the volatile components, as described in EP 0 693 254. These deep-drawn containers can be used in an electrical heating device for killing insects, for example mosquitoes.

In the case where mosquitoes are killed using an electrical heating device, a so-called tablet vaporizer, it is generally known that specifically selected substances, such as cellulose board and cotton board, asbestos, ceramics and/or porous synthetic resins are impregnated with pyrethroid insecticides to obtain insecticide tablets, the insecticides being volatilized by the action of the mosquito killing heating device, which generates a temperature of 120–190° C.

A considerable disadvantage of these tablet vaporizers is the unfavourable ratio between energy input and active compound to be vaporized, since the proportion of active compound relative to the auxiliaries is to be considered as low. Furthermore, the high working temperature of these tablet vaporizers means that only few active compounds are suitable for this purpose in the first place, and that, moreover, these active compounds are released over the predetermined period of action in a non-uniform manner, for system reasons. The period of action of these vaporizer tablets is limited to a maximum of 12 hours. Finally, the unfavourable ratio of active compound/active compound carrier requires a substantial, constantly available stock of vaporizer tablets, which means that large amounts of material are necessary as carriers and packaging material.

The devices which are already widely used for domestic purposes, in which a solution of an insecticidally active compound is vaporized by means of a heated wick (GB 2 153 227), where the active compound is dissolved in a kerosene mixture of saturated aliphatic hydrocarbons which is vaporized electrically by means of the wick, also have considerable disadvantages.

Apart from the fact that these vapour-producing systems also operate at temperatures of between 120 and 190° C., they require a specific distribution system (wick) and considerable amounts of solvents. When the product is used, the superproportional amount of solvent relative to the active compound results in a high concentration of solvents or adjuvants in the room, which, in turn, leads to dirtying of walls and objects in the vicinity of these devices, which has frequently been observed by customers and given cause for complaint.

Other disadvantages of these formulations are the high volume of the solvent containers and the risk of the solvent leaking, which means that there are substantial problems during transport and hazards in use.

Furthermore, EP 0 693 254 mentions gel formulations which have the disadvantage that they persist for a long time indoors and that they additionally consist of very expensive components.

The novel insecticide-comprising gel formulations according to the invention include mixtures which comprise at least one type of a pyrethroid insecticide, a vaporization-controlling substance and an inorganic solid suitable as a gel former.

Suitable active compounds which can be used are the active compounds mentioned in EP 0 693 254.

Particularly suitable here are formulations with the active compound transfluthrin (Bayothrin®, 2,3,5,6-tetrafluorobenzyl (+)-1R-trans-2,2-dimethyl-3-(2,2-dichlorovinyl)cyclopropanecarboxylate) having a reduced active compound content and in combination with novel vaporization-controlling substances, also referred to as vaporization modifiers, which have a strongly reduced risk potential during processing and which are furthermore rapidly degradable indoors.

Preferred novel vaporization modifiers are medicinal white oils CAS No. 8042-47-5 (BP Enerpar M002®) and high-pressure hydrogenated mineral oils CAS No. 8042-47-5 (Enerpar M1930®).

Particular preference is given to naturally regrowing raw materials such as rapeseed oil, rapeseed oil methyl ester and colourless to slightly yellowish Guerbet alcohol of liquid/solid consistency having a very weak intrinsic odour, CAS No.: 67 187-86-0 (Guerbitol 32/36®), colourless to slightly yellowish Guerbet aalcohol of liquid consistency having very weak intrinsic odour=2-hexyldecan-1-ol, CAS No.: 36311-34-9 (Guerbitol 16®).

Particular preference is given to colourless to slightly yellowish Guerbet alcohol of liquid consistency=2-hexyldecan-1-ol, CAS No.: 36311-34-9 (Guerbitol 16®).

The formulations generally comprise between 1.0 and 95% by weight of insecticidally active compound, preferably between 5.0 and 80%, in particular from 20 to 50% by weight.

The formulations furthermore generally comprise between 10 and 90% by weight of vaporization modifiers, preferably between 40 and 80%, and generally between 1 and 12% of gel former, preferably between 6 and 10%.

The ratio of active compound/vaporization modifier in the insecticide-comprising gel formulations according to the invention is between 9 and 0.1; preferably between 2.0 and 0.2.

It is furthermore possible to add organic or inorganic auxiliaries, stabilizers, perfumes and colorants, as described in EP 0 693 254, inter alia, to these mixtures.

The formulations must have an optimum storage stability over a long period of time.

The gel formulations according to the invention are prepared by first stirring at room temperature in a suitable mixing apparatus (planetary paddle mixer) the active compound with the vaporization modifier and stabilizer and, if appropriate, additional solvents, to give a clear solution. Then, the gel former is added under reduced pressure, and the mixture is stirred vigorously until a homogeneous gel is formed. Before the gel former is mixed in to give the final gel product, perfume oils and colorants can optionally be added to the existing clear solution with stirring until the mixture is completely homogeneous.

For use, the film container with the coloured gel is inserted into a heating device whose front is transparent or fitted with an inspection opening.

During the use of the heating device, the content of the film container, which is not visible through a colour marking on the container itself or on the heating device, dries out.

Only the empty film container is still visible through the transparent front of the heating device or through the inspection opening.

A further variant for visual identification of the end point using added colorants may also take the form of a change in colour when the active compounds and, if appropriate, the solvent have vaporized.

The present invention is to be illustrated by the present examples:

EXAMPLE 1
Formulations having Novel Vaporization Modifiers

| Example | Insecticide content | Gel former | Stabilizer | Vaporization modifier |
|---|---|---|---|---|
| 1.1. | 25% Transfluthrin® | 6% Aerosil 200® | 1% BHT | 64% Enerpar M002® |
| 1.2. | 25% Transfluthrin® | 8% Aerosil COK 84® | 1% BHT | 64% Guerbitol 16® |

EXAMPLE 2

The insecticide-comprising gel formulations can be prepared as follows:

2.1

For a 100 kg batch, 25 kg of liquid Transfluthrin® (temperature about 40° C.) are initially charged in a stirring apparatus, 64 kg of Enerpar M002® and 1 kg of BHT are added and the mixture is stirred to give a clear solution. Additionally, it is possible to stir into the formulation preferably the perfume oils aurantiol, citronella oil, C10–C16 aldehyde, birch tar oil, benzyl salicylate, lavender oil or rose oil in combination with, or without, the colorants Hostasol yellow®, Resolin-brilliant red BLS®, 1,4-diaminoanthraquinone, Alizarin VK6/225, Fatty Red HRR®, Fatty Red G®, Solvaperm Green G or Sudan Blue 670®. With rapid stirring, 6 kg of Aerosil 200 are introduced into the clear solution under reduced pressure until a gel has formed.

2.2

For a 100 kg batch, 25 kg of liquid Transfluthrin® (temperature) about 40° C. are initially charged in a stirring apparatus, 64 kg of Guerbitol 16® and 1 kg of BHT are added and the mixture is stirred to give a clear solution. Additionally, it is possible to stir into the formulation preferably the perfume oils aurantiol, citronella oil, C10–C16 aldehyde, birch tar oil, benzyl salicylate, lavender oil or rose oil in combination with, or without, the colorants Hostasol yellow®, Resolin-brilliant red BLS®, 1,4-diaminoanthraquinone, Alizarin VK6/225, Fatty Red HRR®, Fatty Red G®, Solvaperm Green G or Sudan Blue 670®. With rapid stirring, 8 kg of Aerosil COK 84® are introduced into the clear solution under reduced pressure until a gel has formed.

For use, the gel formulations are, depending on the duration of use, filled into deep-drawn or cast containers generally in amounts of 0.2–0.5 g, preferably in amounts of 0.2–0.3 g, and sealed with polypropylene film. Preferred container materials are aluminium, polyester, polyethylene, metals. The dimensions of the container are chosen such that the area of the bottom of the container has the same size as the heating area of the heating device and transfers temperatures of from 70 to 112° C.

The controlled and sustained release of insecticidally active compounds is effected by using Examples 2.1 and 2.2 as follows:

1.6 g of the insecticide-comprising gel formulations are uniformly distributed on the surface of deep-drawn aluminium container having the dimensions (4×2.5×0.4 cm) and sealed with the PP film Walothen C5OSE® or Trespaphan 6ND50®. In a heating device having a temperature of 100–112° C., the container is heated for 8 hours each day, and the release rates of the formulation are determined.

The results of the vaporization tests are shown in Example 3.

EXAMPLE 3

Release Rates of the Formulations from Example 1.1 and 1.2 in [mg/h]

| Heater temperatures: | 105–107° C. |
|---|---|
| Voltage: | 230 V |
| Room temperature: | 20–22° C. |
| Duration of the cycle: | 8 h |
| Cycle pause: | 4 h |
| Weighed-out formulation: | 1.6 g |

| Cycle | Example 1.1 | Example 1.2 |
|---|---|---|
|  | Weight loss per hour in mg | |
| 1 | 4.6 | 4.6 |
| 2 | 4.8 | 4.5 |
| 3 | 4.1 | 4.4 |
| 4 | 4.1 | 4.3 |
| 5 | 3.2 | 4.8 |
| 8 | 3.2 | 4.4 |
| 10 | 3.2 | 4.3 |
| 12 | 3.2 | 4.1 |
| 14 | 2.7 | 4.0 |
| 16 | 2.5 | 3.8 |
| 18 | 2.4 | 3.5 |
| 20 | 2.2 | 3.5 |
| 22 | 2.0 | 3.9 |
| 24 | 2.0 | 3.8 |
| 26 | 2.0 | 3.4 |
| 28 | 2.1 | 3.3 |
| 30 | 1.4 | 2.9 |
| 32 | 1.2 | 2.6 |
| 34 | 1.3 | 2.5 |
| 36 | 1.2 | 2.7 |
| 38 | 1.0 | 2.3 |
| 40 | 1.1 | 2.2 |
| 42 | 0.9 | 2.2 |
| 44 | 0.8 | 1.6 |
| 46 | 0.8 | 1.3 |

-continued

| Cycle | Example 1.1 | Example 1.2 |
|---|---|---|
| | Weight loss per hour in mg | |
| 48 | 0.8 | 1.2 |
| 50 | 0.6 | 1.0 |

EXAMPLE 4
Biological Effect on Mosquitoes of the Variety Aedes Aegypti, Sensitive Room size: 36 m³
Kind of room: 1 window, open
temperature: 20–28° C.
rel. humidity in the room: 17–34%
heater temperature: 105–110° C.
content of active compound: 25% of transfluthrin
weighed-out formulation: 1.6 g

| Duration of operation/ Examination after days (hours) | Mosquitoes released after hours | Formulation 1.1 KD effect after min or h 50% | 100% | % dead after 9 h | 24 h | Formulation 1.2 KD effect after min or h 50% | 100% | % dead after 9 h | 24 h |
|---|---|---|---|---|---|---|---|---|---|
| 1 day | 0 | 1 h 03' | 1 h 15' | 100 | 100 | 1 h 14' | 2 h 02' | 100 | 100 |
| | 1 | 19' | 1 h 05' | 100 | 100 | 39' | 59' | 100 | 100 |
| | 2 | 10' | 17' | 100 | 100 | 11' | 16' | 100 | 100 |
| | 3 | 4' | 7' | 100 | 100 | 32' | 45' | 100 | 100 |
| | 4 | 4' | 7' | 100 | 100 | 9' | 17' | 100 | 100 |
| | 5 | 4' | 6' | 100 | 100 | 7' | 21' | 100 | 100 |
| | 6 | 3' | 5' | 100 | 100 | 12' | 22' | 100 | 100 |
| | 7 | 4' | 5' | 100 | 100 | 15' | 24' | 100 | 100 |
| 8 hours | 8 | 4' | 5' | 100 | 100 | 7' | 18 | 100 | 100 |
| 2 days | 0 | 53' | 1 h 21' | 100 | | 1 h 02' | 1 h 34' | 100 | |
| | 1 | 29' | 1 h 02' | 100 | | 1 h 04' | 2 h 20' | 100 | |
| | 2 | 21' | 35' | 100 | | 1 h 03' | 1 h 30' | 100 | |
| | 3 | 13' | 23' | 100 | | 44' | 1 h 35' | 100 | |
| | 4 | 14' | 24' | 100 | | 37 | 1 h 12' | 100 | |
| | 5 | 7' | 13' | 100 | | 35' | 1 h 14' | 100 | |
| | 6 | 9' | 20' | 100 | | 23' | 40' | 100 | |
| | 7 | 7' | 13' | 100 | | 26' | 45' | 100 | |
| 16 hours | 8 | 5' | 8' | 100 | | 9' | 14' | 100 | |
| 7 days | 0 | 41' | 52' | 100 | 100 | 1 h 10' | 1 h 34' | 100 | 100 |
| | 1 | 24' | 42' | 100 | 100 | 39' | 1 h 24' | 100 | 100 |
| | 2 | 8' | 14' | 100 | 100 | 34' | 1 h 03' | 100 | 100 |
| | 3 | 8' | 16' | 100 | 100 | 15' | 54' | 100 | 100 |
| | 4 | 7' | 15' | 100 | 100 | 18' | 30' | 100 | 100 |
| | 5 | 8' | 17' | 100 | 100 | 24' | 41' | 100 | 100 |
| | 6 | 8' | 16' | 100 | 100 | 19' | 31' | 100 | 100 |
| | 7 | 7' | 14' | 100 | 100 | 16' | 44' | 100 | 100 |
| 56 hours | 8 | 6' | 11' | 100 | 100 | 7' | 12' | 100 | 100 |
| 13 days | 0 | 30' | 43' | 100 | 100 | 29' | 48' | 100 | 100 |
| | 1 | 6' | 11' | 100 | 100 | 8' | 13' | 100 | 100 |
| | 2 | 4' | 8' | 100 | 100 | 6' | 10' | 100 | 100 |
| | 3 | 3' | 4' | 100 | 100 | 4' | 9' | 100 | 100 |
| | 4 | 2' | 5' | 100 | 100 | 4' | 8' | 100 | 100 |
| | 5 | 3' | 6' | 100 | 100 | 7' | 22' | 100 | 100 |
| | 6 | 2' | 6' | 100 | 100 | 6' | 12' | 100 | 100 |
| | 7 | 2' | 7' | 100 | 100 | 5' | 8' | 100 | 100 |
| 104 hours | 8 | 2' | 6' | 100 | 100 | 5' | 8' | 100 | 100 |
| 20 days | 0 | 42' | 57' | 100 | 100 | 38' | 55' | 100 | 100 |
| | 1 | 5' | 11' | 100 | 100 | 3' | 7' | 100 | 100 |
| | 2 | 5' | 11' | 100 | 100 | 2' | 6' | 100 | 100 |
| | 3 | 4' | 8' | 100 | 100 | 2' | 4' | 100 | 100 |
| | 4 | 5' | 7' | 100 | 100 | 2' | 4' | 100 | 100 |
| | 5 | 6' | 9' | 100 | 100 | 2' | 6' | 100 | 100 |
| | 6 | 5' | 8' | 100 | 100 | 2' | 5' | 100 | 100 |
| | 7 | 4' | 8' | 100 | 100 | 2' | 7' | 100 | 100 |
| 160 hours | 8 | 5' | 7' | 100 | 100 | 2' | 6' | 100 | 100 |
| 27 days | 0 | 1 h 28' | 1 h 53' | 100 | 100 | 42' | 52' | 100 | 100 |
| | 1 | 1 h 13' | 2 h 05' | 100 | 100 | 35' | 49' | 100 | 100 |
| | 2 | 1 h 01' | 1 h 35' | 100 | 100 | 10' | 50' | 100 | 100 |
| | 3 | 40' | 1 h 13' | 100 | 100 | 7' | 14' | 100 | 100 |
| | 4 | 23' | 43' | 100 | 100 | 7' | 12' | 100 | 100 |
| | 5 | 33' | 53' | 100 | 100 | 8' | 15' | 100 | 100 |
| | 6 | 8' | 18' | 100 | 100 | 4' | 8' | 100 | 100 |
| | 7 | 20' | 58' | 100 | 100 | 3' | 5' | 100 | 100 |
| 216 hours | 8 | 7' | 11' | 100 | 100 | 3' | 5' | 100 | 100 |
| 35 days | 0 | 1 h 25' | 2 h 20' | 100 | 100 | 1 h 00' | 1 h 13' | 100 | 100 |
| | 1 | 43' | 1 h 15' | 100 | 100 | 11' | 43' | 100 | 100 |

-continued

| Duration of operation/ Examination after days | Mosquitoes released | Formulation 1.1 | | | | Formulation 1.2 | | | |
|---|---|---|---|---|---|---|---|---|---|
| | | KD effect after min or h | | % dead after | | KD effect after min or h | | % dead after | |
| (hours) | after hours | 50% | 100% | 9 h | 24 h | 50% | 100% | 9 h | 24 h |
| | 2 | 28' | 1 h 03' | 100 | 100 | 5' | 10' | 100 | 100 |
| | 3 | 43' | 1 h 03' | 100 | 100 | 3' | 7' | 100 | 100 |
| | 4 | 13' | 1 h 18' | 100 | 100 | 3' | 7' | 100 | 100 |
| | 5 | 15' | 58' | 100 | 100 | 2' | 7' | 100 | 100 |
| | 6 | 20' | 1 h 05' | 100 | 100 | 3' | 18' | 100 | 100 |
| | 7 | 8' | 28' | 100 | 100 | 2' | 9' | 100 | 100 |
| 280 hours | 8 | 10' | 48' | 100 | 100 | 2' | 7' | 100 | 100 |
| 42 days | 0 | 2 h 23' | 3 h 05' | 100 | 100 | 53' | 1 h 28' | 100 | 100 |
| | 1 | 2 h 43' | 3 h 15' | 100 | 100 | 1 h 05' | 1 h 45' | 100 | 100 |
| | 2 | 1 h 43' | 2 h 48' | 100 | 100 | 53' | 1 h 35' | 100 | 100 |
| | 3 | 1 h 53' | 3 h 50' | 100 | 100 | 1 h 00' | 1 h 55' | 100 | 100 |
| | 4 | 1 h 20' | 2 h 28' | 100 | 100 | 48' | 1 h 25' | 100 | 100 |
| | 5 | 45' | >4 h | 98 | 100 | 33' | 48' | 100 | 100 |
| | 6 | 38' | 1 h 28' | 100 | 100 | 12' | 55' | 100 | 100 |
| | 7 | 48' | >2 h | 90 | 100 | 14' | 48' | 100 | 100 |
| 336 hours | 8 | >1 h | >1 h | 45 | 100 | 6' | 10' | 100 | 100 |
| 48 days | 0 | 1 h 42' | 2 h 40' | 100 | | 1 h 40' | 2 h 20' | 100 | |
| | 1 | 2 h 45' | 3 h 50' | 100 | | 1 h 30' | 2 h 15' | 100 | |
| | 2 | 1 h 43' | 2 h 55' | 100 | | 1 h 00' | 2 h 18' | 100 | |
| | 3 | 1 h 45' | 2 h 48' | 100 | | 1 h 03' | 2 h 05' | 100 | |
| | 4 | 1 h 23' | 2 h 13' | 100 | | 53' | 1 h 48' | 100 | |
| | 5 | 1 h 48' | >4 h | 95 | | 40' | 1 h 45' | 100 | |
| | 6 | 1 h 20' | >3 h | 88 | | 35' | 1 h 00' | 100 | |
| | 7 | 39' | >2 h | 90 | | 9' | 48' | 100 | |
| 384 hours | 8 | >1 h | >1 h | 60 | | 8' | >1 h | 90 | |

Based on the present results, the biological activity of the formulations mentioned here is sufficient.

What is claimed is:

1. A gel formulation useful in the controlled and sustained release of a vapor containing at least one insecticidally active compound comprising:
    (a) from about 1.0% to about 95% by weight of at least one pyrethroid;
    (b) from about 1% by weight to about 12% by weight of a gel former; and
    (c) from about 10% by weight to about 90% by weight of a vaporization modifier selected from the group consisting of medicinal white oils and high-pressure hydrogenated mineral oils having CAS No. 8042-47-5, rapeseed oil, rapeseed oil methyl ester, Guerbet alcohols and combinations and mixtures thereof,
wherein said vaporization modifier is present in an amount sufficient to modify the vaporization rate of said gel formulation at an operating temperature from about 70° C. to about 110° C.; and wherein said gel formulation forms said vapor containing at least one pyrethroid upon heating to said operating temperature, whereby surfaces exposed to said vapor remain substantially free of residues of said vaporization modifier during use of said gel formulation.

2. The gel formulation of claim 1, wherein said vaporization modifier is selected from the group consisting of Guerbet alcohols having CAS No. 67187-86-0 or CAS No. 36311-34-9, and combinations and mixtures thereof.

3. The gel formulation of claim 1, wherein said pyrethroid is prallethrin.

4. The gel formulation of claim 1, wherein said pyrethrin is 3-allyl-2-methyleyelopent-2-en-4-on-1-yl D-cis/trans-chrysanthemate.

5. The gel formulation of claim 1, wherein said pyrethrin is 1-ethinyl-2-methyl-2-pentenyl 2,2 dimethyl-3-(2-methyl-1-propenyl)-cyclopropane-carboxylate.

6. The gel formulation of claim 1, wherein said at least one insecticidally active compound comprises a natural pyrethrum.

7. The gel formulation of claim 1, wherein said pyrethroid comprises from about 5.0% to about 80% by weight of said gel formulation.

8. The gel formulation of claim 7, wherein said pyrethroid comprises from about 20% to about 50% by weight of said gel formulation.

9. The gel formulation of claim 1, wherein said vaporization modifier comprises from about 40% by weight to about 80% by weight of the formulation.

10. The gel formulation of claim 1, wherein said gel former comprises from about 6% by weight to about 10% by weight of the formulation.

11. The gel formulation of claim 1, wherein the ratio of the total weight of said pyrethroid in said gel formulation to the total weight of said vaporization modifiers is from about 9 to about 0.1.

12. The gel formulation of claim 11, wherein said ratio is from about 2.0 to 0.2.

13. The gel formulation of claim 1, wherein said pyrethroid comprises transfluthrin.

14. The gel formulation of claim 1 further comprising a container for holding said gel formulation during heating to a temperature from about 70° C. to about 110° C.

15. The gel formulation of claim 14, further comprising a heating device adapted to heat said gel formulation in said container to said temperature.

* * * * *